US010088492B2

(12) United States Patent
Wegener et al.

(10) Patent No.: US 10,088,492 B2
(45) Date of Patent: Oct. 2, 2018

(54) SYSTEM AND METHOD FOR DETECTING MINIMUM HEMATOCRIT WITH IRRADIATION RECEIVERS DURING EXTRACORPOREAL PHOTOPHERESIS

(71) Applicant: Fenwal, Inc., Lake Zurich, IL (US)

(72) Inventors: Christopher J Wegener, Libertyville, IL (US); Katherine N Radwanski, Highland Park, IL (US)

( * ) Notice: Subject to any disclaimer, the term of this patent is extended or adjusted under 35 U.S.C. 154(b) by 451 days.

(21) Appl. No.: 14/976,950

(22) Filed: Dec. 21, 2015

(65) Prior Publication Data

US 2016/0195555 A1 Jul. 7, 2016

Related U.S. Application Data

(60) Provisional application No. 62/099,745, filed on Jan. 5, 2015.

(51) Int. Cl.
*A61M 37/00* (2006.01)
*G01N 33/80* (2006.01)
(Continued)

(52) U.S. Cl.
CPC ........... *G01N 33/80* (2013.01); *A61M 1/0209* (2013.01); *A61M 1/3683* (2014.02);
(Continued)

(58) Field of Classification Search
CPC ..... G01N 33/80; G01N 21/33; A61M 1/3681; A61M 1/3683; A61M 1/0209;
(Continued)

(56) References Cited

U.S. PATENT DOCUMENTS 5,360,542 A 11/1994 Williamson et al.
5,868,696 A 2/1999 Giesler et al.
(Continued)

FOREIGN PATENT DOCUMENTS

EP 1066842 A2 1/2001
EP 1867355 A1 12/2007
(Continued)

OTHER PUBLICATIONS

Extended European Search Report for App. No. 16150054.1, dated May 20, 2016, 9 pages.
(Continued)

*Primary Examiner* — Philip R Wiest
(74) *Attorney, Agent, or Firm* — Hanna Yoon; Scott M. Day

(57) ABSTRACT

An irradiation device for photopheresis, comprising an exposure chamber configured to receive an illumination container holding a target cell suspension, an irradiation transmitter configured to irradiate the illumination container and target cell suspension, an irradiation receiver configured to detect absorption of radiation from the irradiation transmitter, and a processing circuit coupled to the irradiation receiver and configured to determine whether a hematocrit of the target cell suspension exceeds a predetermined threshold hematocrit and to treat the target cell suspension with a treatment dosage of radiation if the predetermined threshold is exceeded.

16 Claims, 7 Drawing Sheets

(51) Int. Cl.
*A61M 1/02* (2006.01)
*A61M 1/36* (2006.01)
*G01N 21/33* (2006.01)
*A61L 2/10* (2006.01)

(52) U.S. Cl.
CPC .......... *A61M 1/3693* (2013.01); *G01N 21/33* (2013.01); *A61L 2/10* (2013.01); *A61L 2202/22* (2013.01); *A61M 2205/051* (2013.01); *A61M 2205/053* (2013.01); *A61M 2230/207* (2013.01); *G01N 2201/061* (2013.01); *G01N 2201/12* (2013.01)

(58) Field of Classification Search
CPC .......... A61M 1/3693; A61M 2205/051; A61M 2205/053; A61M 2230/207; A61L 2/10; A61L 2202/22
See application file for complete search history.

(56) References Cited

U.S. PATENT DOCUMENTS

| | | | |
|---|---|---|---|
| 6,027,657 A | 2/2000 | Min et al. | |
| 6,219,584 B1 | 4/2001 | Lee | |
| 7,433,030 B2 * | 10/2008 | Waldo | A61L 2/0011 356/218 |
| 2013/0197419 A1 | 8/2013 | Min et al. | |

FOREIGN PATENT DOCUMENTS

| | | |
|---|---|---|
| EP | 2620171 A1 | 7/2013 |
| EP | 2813253 A2 | 12/2014 |
| WO | 2002088897 A2 | 11/2002 |
| WO | 2002088930 A1 | 11/2002 |
| WO | 2009005853 A1 | 1/2009 |
| WO | 2014123521 A1 | 8/2014 |

OTHER PUBLICATIONS

Peritt, "Potential Mechanisms of Photopheresis in Hematopoietic Stem Cell Transplantation," Biology of Blood and Marrow Transplantation 12:7-12 (2006).

* cited by examiner

SYSTEM AND METHOD FOR DETECTING MINIMUM HEMATOCRIT WITH IRRADIATION RECEIVERS DURING EXTRACORPOREAL PHOTOPHERESIS

CROSS-REFERENCE TO RELATED APPLICATIONS

This application claims the benefit of U.S. Provisional Patent App. No. 62/099,745 filed Jan. 5, 2015, which is expressly incorporated herein by reference in its entirety.

FIELD OF THE DISCLOSURE

The present disclosure is directed to a method for performing extracorporeal photopheresis of target cells and, more particularly, to a system and method of detecting hematocrit with irradiation receivers as part of a photopheresis treatment.

BACKGROUND

Whole blood is made up of various cellular and non-cellular components such as red cells, white cells and platelets suspended in its liquid component, plasma. Whole blood may be separated into its constituent components (cellular, liquid or other), and the separated component may be administered to a patient in need of that particular component.

The administration of blood and/or blood components is common in the treatment of patients suffering from disease. Rather than infuse whole blood, individual components may be administered to the patient(s) as their needs require. For example, administration (infusion) of platelets may often be prescribed for cancer patients whose ability to make platelets has been compromised by chemotherapy. Infusion of white blood cells (i.e., mononuclear cells) after the cells have undergone some additional processing or treatment may also be prescribed for therapeutic reasons, including treatment of diseases that specifically involve the white blood cells. Thus, it may be desirable to separate and collect the desired blood component from whole blood and then treat the patient with the specific blood component. The remaining components may be returned to the donor or retained for other uses.

There are several diseases or disorders which are believed to primarily involve mononuclear cells, such as cutaneous T-cell lymphoma, organ allograft rejection after transplantation and autoimmune diseases such as rheumatoid arthritis and systemic sclerosis, among others.

Cutaneous T-cell lymphoma (CTCL) is a term that is used to describe a wide variety of disorders. Generally, CTCL is a type of cancer of the immune system where T-cells (a type of mononuclear cell) mutate or grow in an uncontrolled way, migrate to the skin and form itchy, scaly plaques or patches. More advanced stages of the disease also affect the lymph nodes. Therapeutic treatment options for CTCL have previously been limited. While chemotherapy has been utilized, this particular form of treatment also has many associated undesirable side effects, such as lowered resistance to infection, bleeding, bruising, nausea, infertility and hair loss, just to name a few.

Organ allograft rejection may be characterized as the rejection of tissues that are foreign to a host, including transplanted cardiac tissue as well as lung, liver and renal transplants. Immunosuppression drug therapy following transplantation is common. However, there are potential drawbacks including reoccurring infection due to the compromised competence of the immune system caused by this type of therapy.

Similarly, graft versus host disease (GVHD) is a complication that can occur after a stem cell or bone marrow transplant in which the newly transplanted material attacks the transplant recipient's body. The differences between the donor's cells and recipient's tissues often cause T-cells from the donor to recognize the recipient's body tissues as foreign, thereby causing the newly transplanted cells to attack the recipient. GVHD may complicate stem cell or bone marrow transplantation, thereby potentially limiting these life-saving therapies. Therefore, after a transplant, the recipient is usually administered a drug that suppresses the immune system, which helps reduce the chances or severity of GVHD.

Autoimmune diseases, including rheumatoid arthritis (RA) and progressive systemic sclerosis (PSS), can be characterized by an overactive immune system which mistakes the body's own tissues as being a foreign substance. As a result, the body makes autoantibodies that attack normal cells and tissues. At the same time, regulatory T-cells, which normally function to regulate the immune system and suppress excessive reactions or autoimmunity, fail in this capacity. This may lead to among other things, joint destruction in RA and inflammation of the connective tissue in PSS.

SUMMARY

According to an exemplary embodiment, the present disclosure is directed to an irradiation device for photopheresis, comprising an exposure chamber configured to receive an illumination container holding a target cell suspension, an irradiation transmitter configured to irradiate the illumination container and target cell suspension, an irradiation receiver configured to detect absorption of radiation from the irradiation transmitter, and a processing circuit coupled to the irradiation receiver and configured to determine whether a hematocrit of the target cell suspension exceeds a predetermined threshold hematocrit and to treat the target cell suspension with a treatment dosage of radiation if the predetermined threshold is exceeded.

According to an exemplary embodiment, the present disclosure is directed to a method for detecting hematocrit during an extracorporeal photopheresis procedure, comprising the steps of providing an exposure chamber configured to receive an illumination container holding a target cell suspension containing a selected amount of a photoactivation agent, providing an irradiation device having an irradiation transmitter configured to irradiate contents within the illumination container, wherein the irradiation device contains at least one irradiation receiver, irradiating the target cell suspension with the irradiation device while detecting hematocrit with the irradiation receivers, and providing a response action when the irradiation receivers detect a hematocrit below a minimum acceptable hematocrit.

BRIEF DESCRIPTION OF THE DRAWINGS

Features, aspects, and advantages of the present embodiments will become apparent from the following description, appended claims, and the accompanying exemplary embodiments shown in the drawings, which are briefly described below.

DETAILED DESCRIPTION

Figure 1:
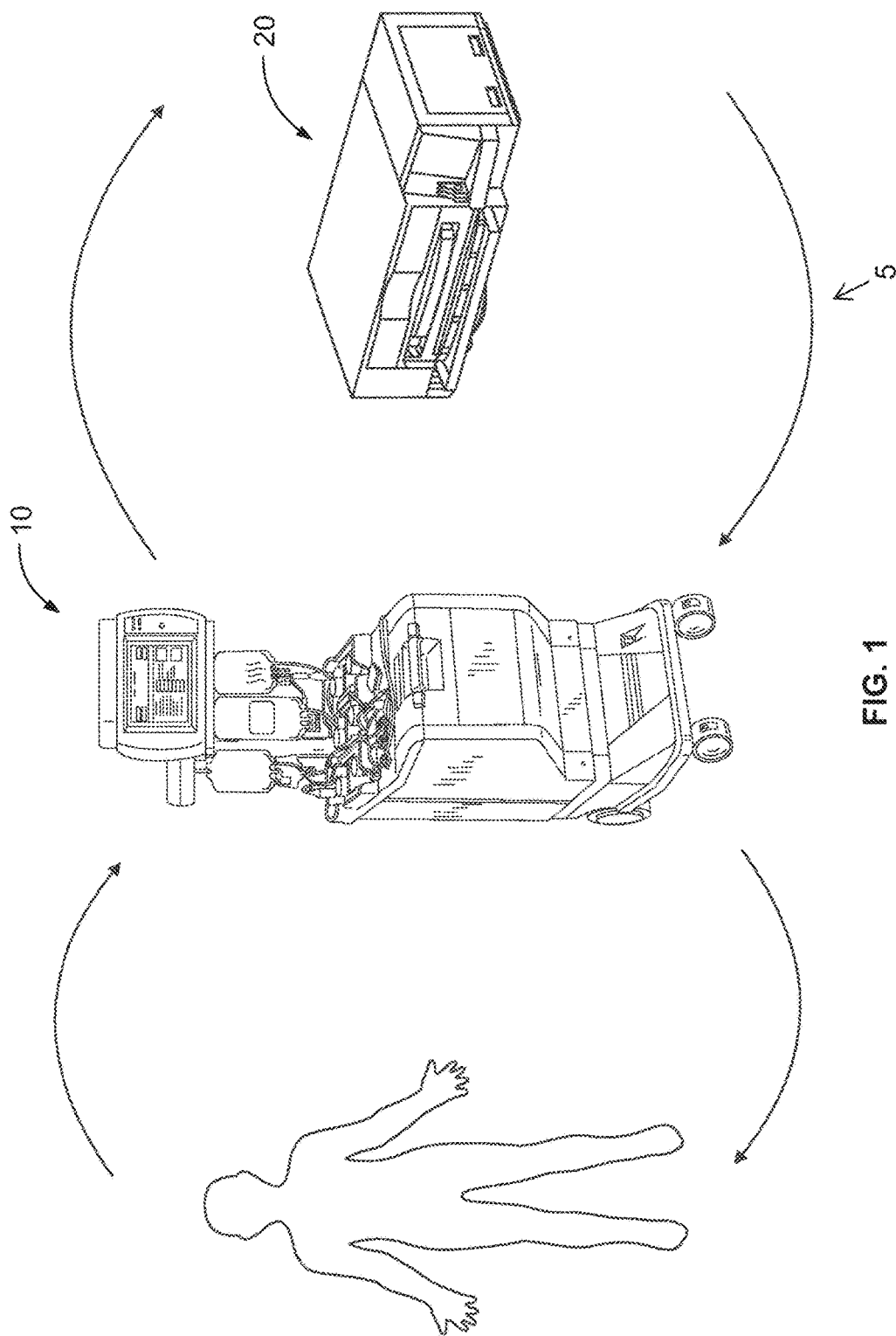
FIG. 1 is a diagram generally showing the mechanical components of a photopheresis treatment device, according to an exemplary embodiment.

There are several aspects of the present subject matter which may be embodied separately or together in the devices and systems described and claimed below. These aspects may be employed alone or in combination with other aspects of the subject matter described herein, and the description of these aspects together is not intended to preclude the use of these aspects separately or the claiming of such aspects separately or in different combinations as set forth in the claims appended hereto.

Where existing therapies for treating one or more diseases may result in certain unintended side effects, additional treatment may be desired or required. One procedure which has been shown to be effective in the treatment of diseases and/or the side effects of existing therapies involving mononuclear cells is extracorporeal photopheresis or "ECP". Extracorporeal photopheresis (also sometimes referred to as extracorporeal photochemotherapy) is a process that includes: (1) collection of mononuclear cells (MNC) from a patient, (2) photoactivation treatment of the collected MNC cells; and (3) re-infusion of the treated cells (MNC) back to the patient. More specifically, ECP involves the extracorporeal exposure of peripheral blood mononuclear cells combined with a photoactive compound, such as 8-methoxypsoralen or "8-MOP" which is then photoactivated by ultraviolet light, followed by the re-infusion of the treated mononuclear cells. The combination of 8-MOP and UV radiation may cause apoptosis or programmed cell death of ECP-treated T-cells.

During ECP treatment, photoactivation is known to cause 8-MOP to irreversibly covalently bind to the DNA strands contained in the T-cell nucleus. When the photochemically damaged T-cells are reinfused, cytotoxic effects may be induced. For example, a cytotoxic T-cell or "CD8+ cell" releases cytotoxins when exposed to infected or damaged cells or otherwise attacks cells carrying certain foreign or abnormal molecules on their surfaces. The cytotoxins target the damaged cell's membrane and enter the target cell, which eventually leads to apoptosis or programmed cell death of the targeted cell. In other words, after the treated mononuclear cells are returned to the body, the immune system recognizes the dying abnormal cells and begins to produce healthy lymphocytes (T-cells) to fight against those cells.

Extracorporeal photopheresis may also induce monocytes (a type of mononuclear cell) to differentiate into dendritic cells capable of phagocytosing and processing apoptotic T-cells. When these activated dendritic cells are re-infused into systemic circulation, they may cause a systemic cytotoxic CD8+T-lymphocyte-mediated immune response to the processed apoptotic T-cell antigens like that described above.

ECP may also result in an immune tolerant response in the patient. For example, in the case of graft versus-host disease, the infusion of apoptotic cells may stimulate regulatory T-cell generation, inhibit inflammatory cytokine production, cause the deletion of effective T-cells and result in other responses. See Peritt, "Potential Mechanisms of Photopheresis in Hematopoietic Stem Cell Transplantation," Biology of Blood and Marrow Transplantation 12:7-12 (2006). While presently the theory of an immune tolerant response appears to be among the leading explanations, there exist still other theories as to the mechanism of action of ECP relative to graft-versus-host disease, as well as other disease states.

In performing an ECP procedure for MNCs, it is desirable to deliver the proper dose of light energy to the photoactivatable material in the suspension within which the MNCs are suspended, particularly if the suspension includes material (such as red blood cells) that is not substantially transparent to light so that it attenuates the light energy intended for photoactivation. The proper dose may be determined and administered by the use of a hem atocrit sensor and algorithm that utilizes information regarding thickness, hematocrit, and light transmittance values of the suspension.

In the absence of a hematocrit sensor to determine hematocrit, the UV dose may also be monitored by UV irradiation receivers (e.g., light sensors) that are angled to detect UV light emitted from UV transmitters (e.g., light source such as light bulbs) and UV light reflected from a mirrored surface behind each transmitter, (e.g., set of bulbs) (and presumably less light is reflected back by virtue of the treated cell product absorbing light). If the product hematocrit is too high, monitoring by UV irradiation receivers (e.g., light sensors) alone may not fully account for the UV light being absorbed by the red cells and plasma and may therefore require operators or the photopheresis system to adjust the product hematocrit via dilution to a sufficiently low level to allow for adequate absorption of energy by the photoactivatable substrate.

Some embodiments may enable a determination of whether a MNC product hematocrit is above minimum hematocrit values to optimize levels of irradiation delivered to the target cells.

Some embodiments may enable determination of hematocrit without the presence of a dedicated hematocrit sensor or cell counter.

Some embodiments may detect a lower limit of hematocrit hematocrit in an offline photopheresis method to avoid over-irradiation of the product.

In some embodiments, over-irradiation of MNCs during an ECP procedure may be avoided, so that cells do not prematurely undergo apoptosis or necrosis prior to re-entering the patient's bloodstream, thereby minimizing compromise to the intended immune response and the therapeutic effects of the ECP procedure.

Figure 2:
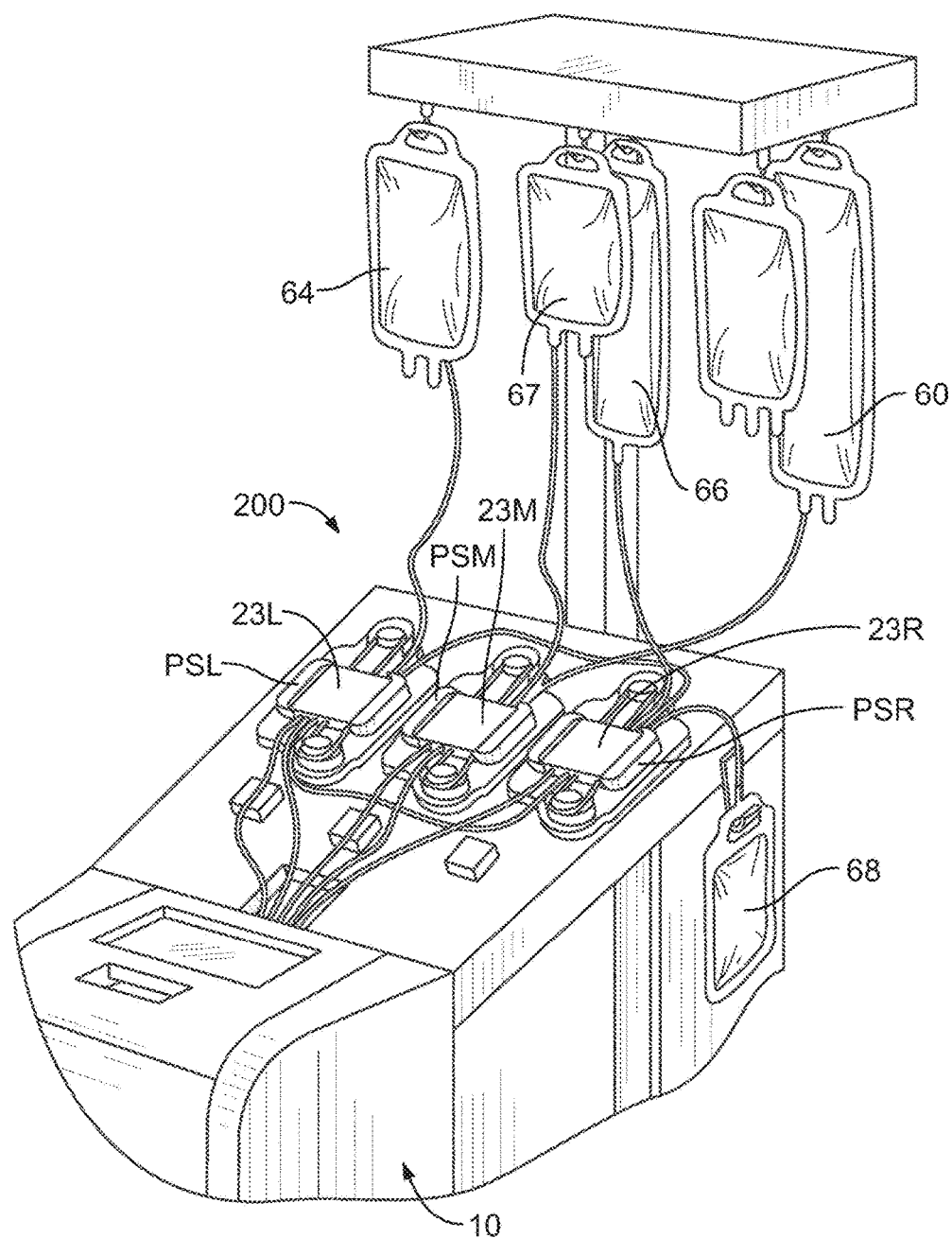
FIG. 2 is a partial perspective view of an apheresis separator useful in the methods and systems described herein, according to an exemplary embodiment.
Figure 4:
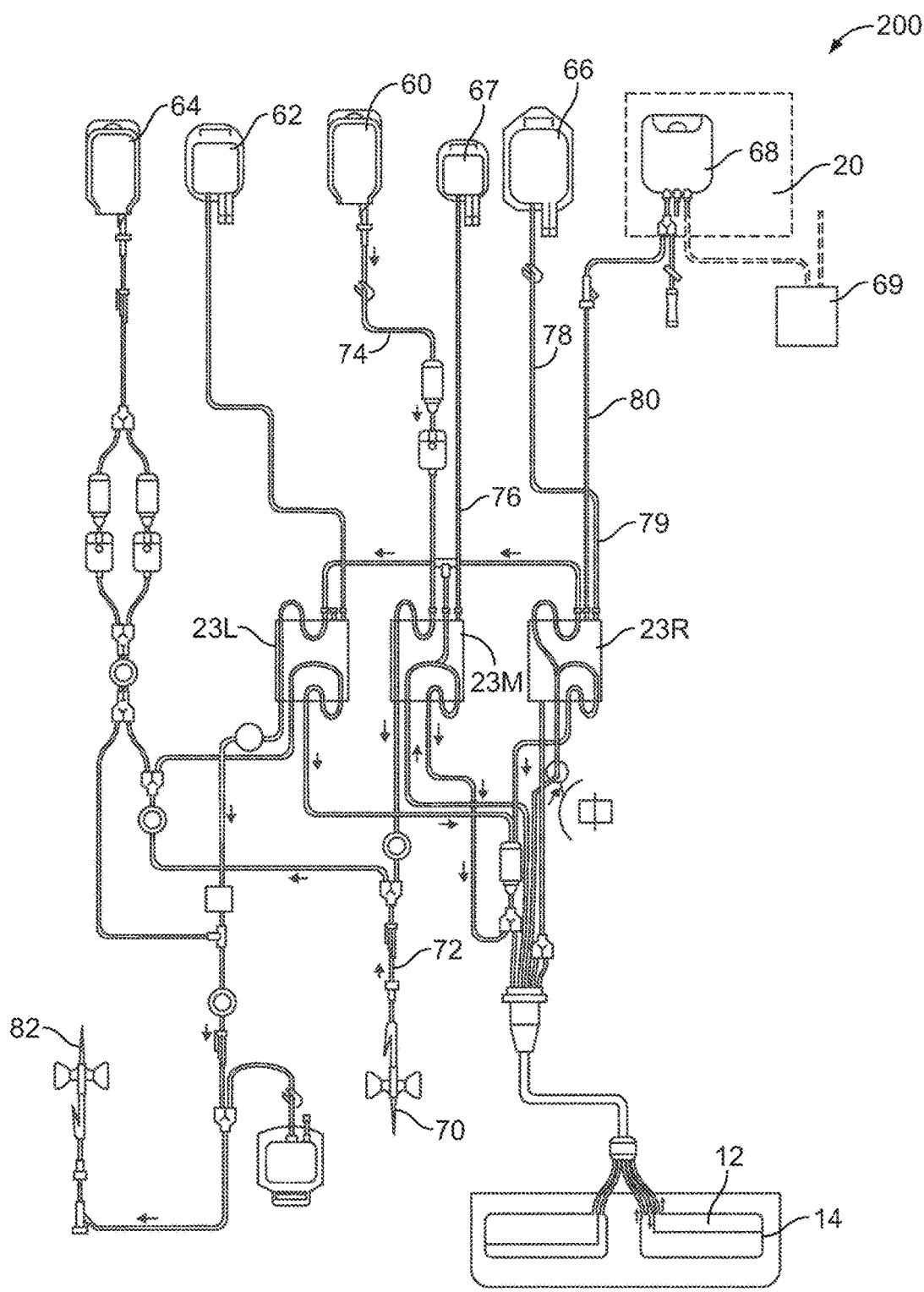
FIG. 4 is a diagram of the fluid circuit useful in the collection, treatment and reinfusion of target cells, according to an exemplary embodiment.

FIG. 1 shows, in general, the mechanical components that make up an ECP system 5 and that may be used in one or more of the methods described herein. The system 5 may include a separation component 10 and a treatment (i.e., irradiation) component 20. Irradiation component 20 may be independent and housed separately from the separation component 10, or components 20 and 10 may be integrated into a single device. In an embodiment in which components 20 and 10 are housed separately, the separation device 10 and irradiation device 20 may be located adjacent to each other, allowing an operator or clinician to have access to both devices during a particular treatment procedure. A patient may be connected to a fluid circuit 200 as shown in FIGS. 1, 2, 4 that provides a sterile closed pathway between separation component 10 and irradiation component 20 and may be cooperatively mounted on the hardware of the separation device 10. The separation device 10 may have one or more features of an apheresis device, such as a system marketed as the AMICUS® separator by Fenwal, Inc. of Lake Zurich, Ill., as described in greater detail in U.S. Pat. No. 5,868,696, which is hereby incorporated herein by reference in its entirety, although any suitable separation device may be used. Although the embodiments disclosed herein are described in conjunction with a separation device 10, the present embodiments may be applicable to an irradiation device 20 alone, in which case the target cell population may be provided to the irradiation device 20 subsequent to being collected elsewhere.

With reference to FIG. 1, whole blood may be withdrawn from the patient and introduced into the separation component 10 where the whole blood is separated to provide a target cell population. In one embodiment, the target cell population may be mononuclear cells (MNCs) or MNCs of a particular type (lymphocytes, monocytes, and/or dendritic cells, etc.). Other components separated from the whole blood, such as red blood cells (RBCs), plasma, and/or platelets may be returned to the patient or collected in pre-attached containers of the blood processing set.

The separated target cell population, e.g., mononuclear cells, may then be treated and irradiated in treatment component 20. As discussed above, treatment of mononuclear cells may involve the photoactivation of a photoactive agent that has been combined with the mononuclear cells. Mononuclear cell collections using a device such as the Amicus® are described in greater detail in U.S. Pat. No. 6,027,657, the contents of which are incorporated by reference herein in its entirety. Preferably, the apparatus used for the harvesting, collection and reinfusion of mononuclear cells may be a "multifunctional" automated apheresis device, as is the case with the Amicus® Separator. In other words, the separation component 10 may be a multifunctional automated apparatus that can perform various collection protocols and/or serve multiple purposes, as may be needed by a particular hospital or facility, such that it can be used not only in the systems and methods for performing photopheresis treatment of MNC as described herein, but can also be used for other purposes including the collection of blood and blood components including platelets, plasma, red blood cells, granulocytes and/or perform plasma/RBC exchange, among other functions required by the hospital or medical facility.

Figure 3:
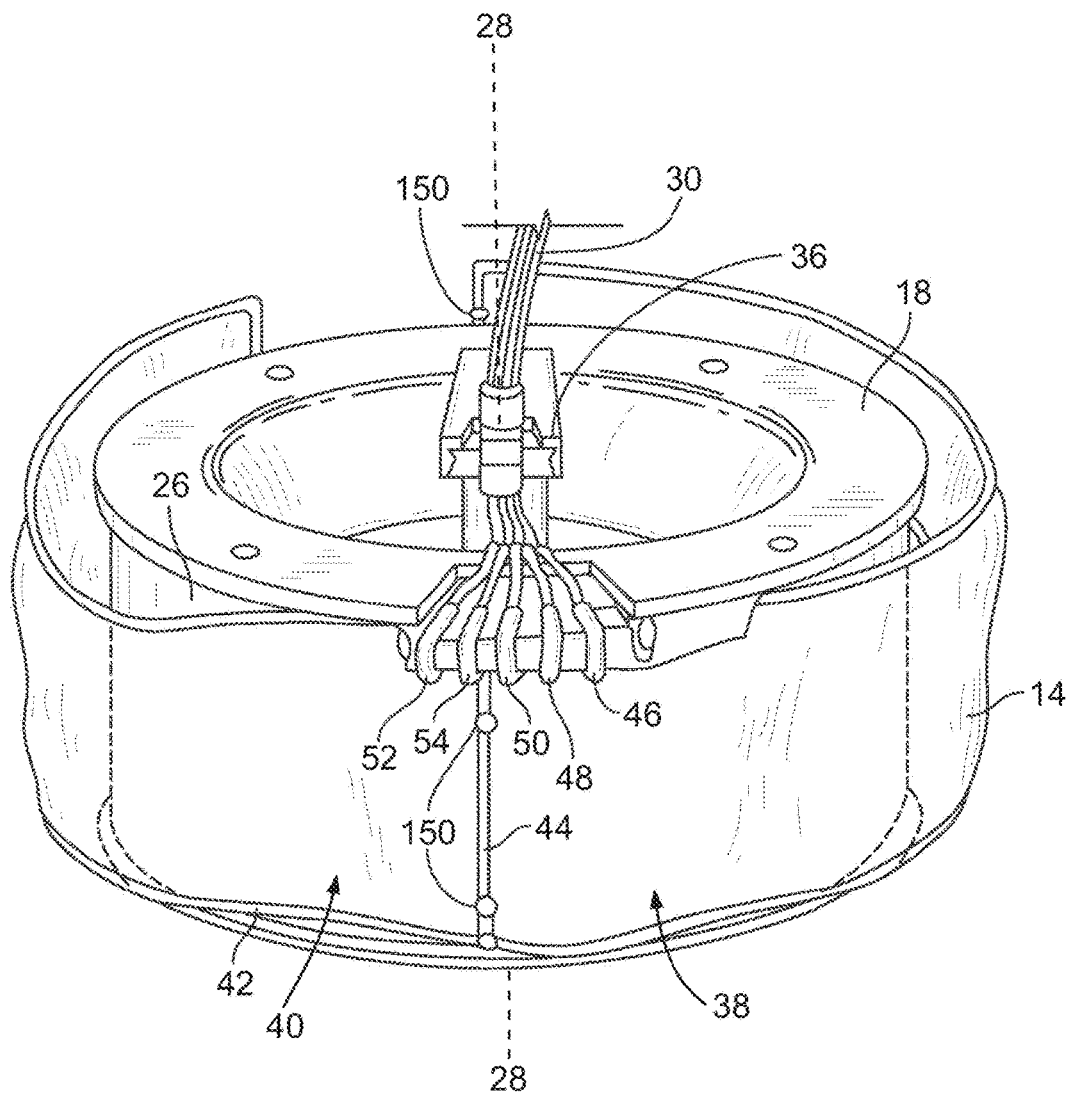
FIG. 3 is a perspective view of a separation chamber of the processing set used with the separator of FIG. 2, according to an exemplary embodiment.

FIGS. 2-4 depict a separator 10 with fluid circuit 200 mounted thereon (FIG. 2), the fluid circuit (FIG. 4) having a blood processing container 14 (FIG. 3) defining a separation chamber 12 suitable for harvesting mononuclear cells (MNC) from whole blood. As shown in FIG. 2, a disposable processing set or fluid circuit 200 (which includes container 14) may be mounted on the front panel of separator 10. The fluid circuit 200 may include a plurality of processing cassettes 23L, 23M and 23R with tubing loops for association with peristaltic pumps on separator 10. Fluid circuit 200 may also include a network of tubing and pre-connected containers for establishing flow communication with the patient and for processing and collecting fluids and blood and blood components, as shown in FIG. 4. As seen in FIGS. 2 and 4, disposable processing set 200 may include a container 60 for supplying anticoagulant, a waste container 62 for collecting waste from one or more steps in the process for treating and washing mononuclear cells, a container 64 for holding saline or other wash or resuspension medium, a container 66 for collecting plasma, a container 68 for collecting the mononuclear cells and, optionally, container 69 for holding the photoactivation agent.

Container 68 may also serve as the illumination container, and the illumination container 68 may be pre-attached to and integral with the disposable set 200. Alternatively, container 68 may be attached to set 200 by known sterile connection techniques, such as sterile docking or the like. In FIG. 2, container 68 is shown as suspended from device 10. However, container 68 may be housed within an adjacent separately housed irradiation device 20 (as shown by broken lines in FIG. 4), thereby eliminating the step of having the operator place container 68 into irradiation device 20. The tubing leading to and/or from container 68 in fluid circuit 200 may be of a sufficient length to reach an irradiation device 20 that is adjacent to but housed separately from the separation device.

With reference to FIG. 4, fluid circuit 200 may include inlet line 72, an anticoagulant (AC) line 74 for delivering AC from container 60, an RBC line 76 for conveying red blood cells from chamber 12 of container 14 to container 67, a platelet poor plasma (PPP) line 78 for conveying PPP to container 66 and line 80 for conveying mononuclear cells to and from blood processing container 14 and collection/illumination container 68. The blood processing set may include one or more venipuncture needle(s) for accessing the circulatory system of the patient. As shown in FIG. 4, fluid circuit 200 may include inlet needle 70 and return needle 82. In an alternative embodiment, a single needle may serve as both the inlet and outlet needle.

Fluid flow through fluid circuit 200 may be driven, controlled and adjusted by a microprocessor-based controller in cooperation with the valves, pumps, weight scales and sensors of device 10 and fluid circuit 200, the details of which are described in the aforementioned U.S. Pat. No. 6,027,657, although any suitable controller may be used.

In accordance with the present disclosure, the fluid circuit may be further adapted for association with the irradiation device 20. One example of a suitable irradiation device is described in U.S. Pat. No. 7,433,030, which is incorporated by reference herein in its entirety, although any irradiation device may be used. The irradiation device 20 may include a tray or other holder for receiving one or more containers during treatment.

Referring to FIG. 3, separation chamber 12 is defined by the walls of a flexible processing container 14 carried within an annular gap defined by a rotating spool element 18 and an outer bowl element (not shown). The blood processing container 14 may take the form of an elongated tube which is wrapped about the spool element 18 before use. The bowl and spool element 18 may be pivoted on a yoke between an upright position and a suspended position. In operation, the centrifuge 10 may rotate the suspended bowl and spool element 18 about an axis 28, creating a centrifugal field within the processing container 14. Details of the mechanism for causing relative movement of the spool 18 and bowl elements as described are disclosed in U.S. Pat. No. 5,360,542 entitled "Centrifuge with Separable Bowl and Spool Elements Providing Access to the Separation Chamber," which is also incorporated herein by reference in its entirety, although any suitable separation mechanism may be used.

Figure 5:
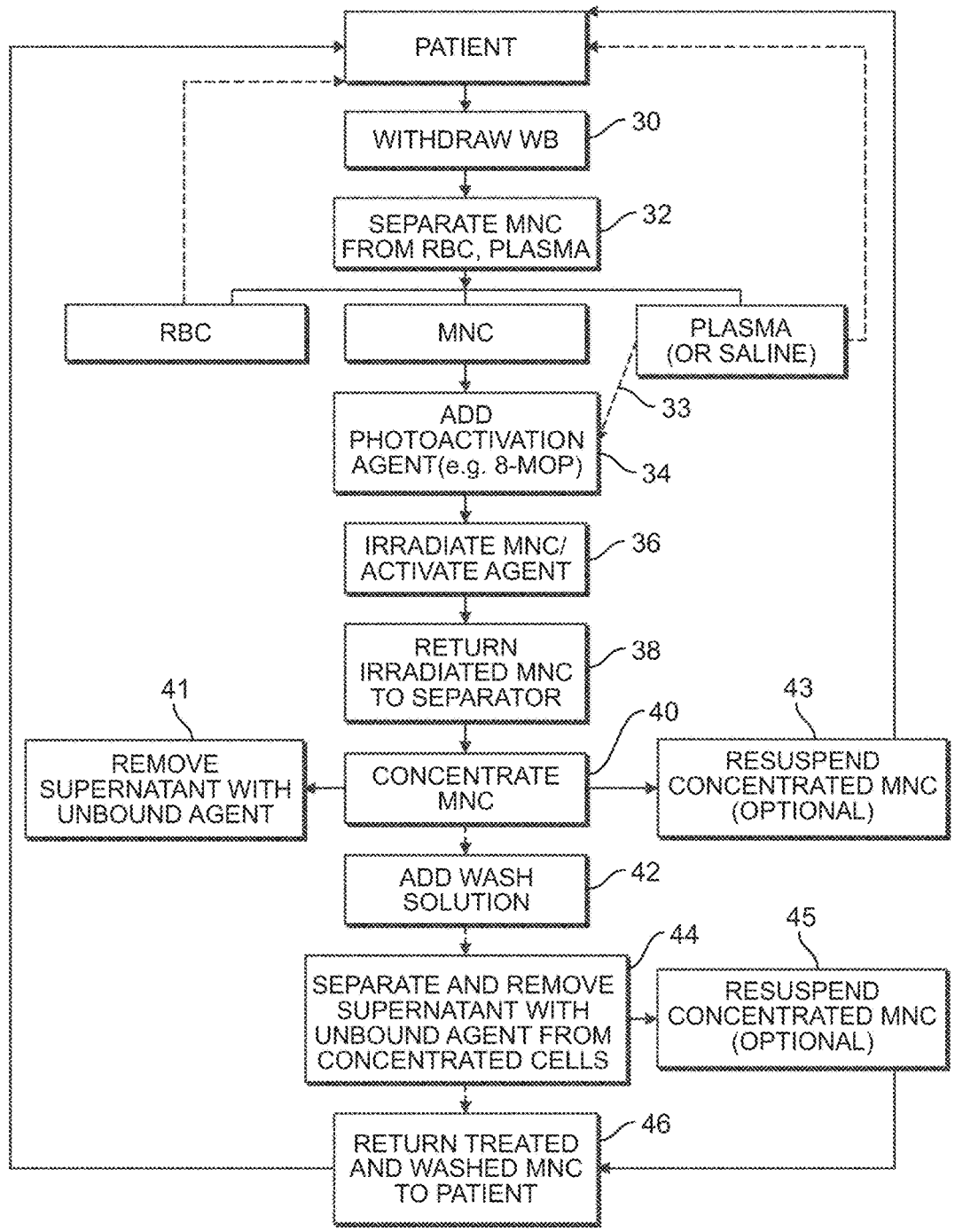
FIG. 5 is a flow chart setting forth a portion of the steps of the method of an online photopheresis treatment, according to an exemplary embodiment.

FIG. 5 depicts one embodiment of an online method of treating mononuclear cells. An "online" photopheresis system includes both the blood separation device and the irradiation device in an integrated system. An online system provides for reinfusion of treated target cells back to the patient. Whole blood may first be withdrawn from a patient (step 30) through inlet needle 70 and introduced into the separation chamber 12 of container 14 of processing set 200, where the whole blood is subjected to a centrifugal field. The centrifugal field may separate the target cell population, i.e., mononuclear cells, from red blood cells, platelets and plasma (step 32). The components such as red blood cells and platelets may be returned to the patient or may be diverted to a container (e.g., container 67) for further processing. Collection of the mononuclear cells may proceed in one or more cycles, with the number of processing cycles conducted in a given therapeutic procedure depending upon the total volume of MNCs to be collected. Although FIG. 5 depicts an online method of treating MNCs, offline methods are available as well. In offline methods, an apheresis device may be used to collect target cells. The collected target cells, typically contained in one or more collection containers, are severed or otherwise separated from the tubing set used during collection, where they are later treated in a separate irradiation or UVA light device followed by subsequent reinfusion of the treated cells to a patient. During such offline methods, when the cells are transferred from the apheresis device to the irradiation device (which device may be located in another room or laboratory), communication with the patient is severed and the cells detached from the patient.

Effective treatment of the MNCs with light may be facilitated by collecting mononuclear cells in a suspension having a suitable hematocrit. The level of hematocrit of the MNC suspension to be treated affects the amount of UV light absorbed by the MNCs, given that the red blood cells in the MNC suspension block at least a portion the UV light from reaching the targeted MNCs. Control of hematocrit may be absent, particularly with systems in which high-precision cell counters or dedicated hematocrit sensors are not integrated, as may be the case. Control of hematocrit may be desirable in cases in which the light source of the irradiation device is configured to irradiate a set intensity of light or limited settings of light intensity values, although hematocrit control may be desirable also in cases in which intensity and exposure settings may readily be adjusted according to hematocrit. It is common for a transmitter (e.g., bank of light bulbs) of an irradiation device to not be adjustable in terms of intensity of emission and therefore may emit a constant intensity of light. If the hematocrit of the suspended MNCs is too high (such that the red blood cells prevent the absorption of light by the MNCs), it may be desired to dilute the mononuclear cells with a diluting solution, such as plasma or saline, as shown in step 33 (FIG. 5), to control the hematocrit so that a desired amount of UV light will reach the targeted MNC. The diluted mononuclear cells (in container 68) may then be combined with the suitable photoactivation agent in step 34. On the other hand, if the hematocrit of the suspended MNCs is too low, the RBCs may not provide adequate blockage of the radiation, resulting in the MNCs becoming over-irradiated during the ECP procedure, leading to the cells prematurely undergoing apoptosis or even necrosis prior to re-entering the patient's bloodstream. In such a case, the intended immune system response may be compromised and may undermine the therapeutic effects of the ECP procedure.

In order to ascertain that the hematocrit of the suspended MNCs is not too low, the UV-A light intensity observed by a UV-A irradiation receiver (e.g., sensor) located within the irradiation device may be used to determine whether a minimum hematocrit has been reached in order to prevent over-irradiation of the MNC product. The previously mentioned U.S. Pat. No. 7,433,030 discloses a UV-A sensor, although any suitable irradiation receiver may be used. The light intensity observed by a UV-A irradiation receiver is dependent on the intensity of the UV-A light emitted by the UV-A light source, by the UV-A light reflected off of the internal surfaces of the exposure chamber, and by the amount or percentage of UV-A absorbed by the MNC suspension, which may include both target and non-target cells as well as the suspension medium. Red blood cells may absorb the majority of the UV-A light emitted by the UV-A light source, with greater absorption by RBCs occurring with increasing thickness of the MNC suspension. Therefore, in order to compensate for light absorbed by non-target material, the UV-A light source may be configured to emit more than 10 times as much UV-A light than is actually absorbed by the target MNCs within the suspension.

Figure 6:
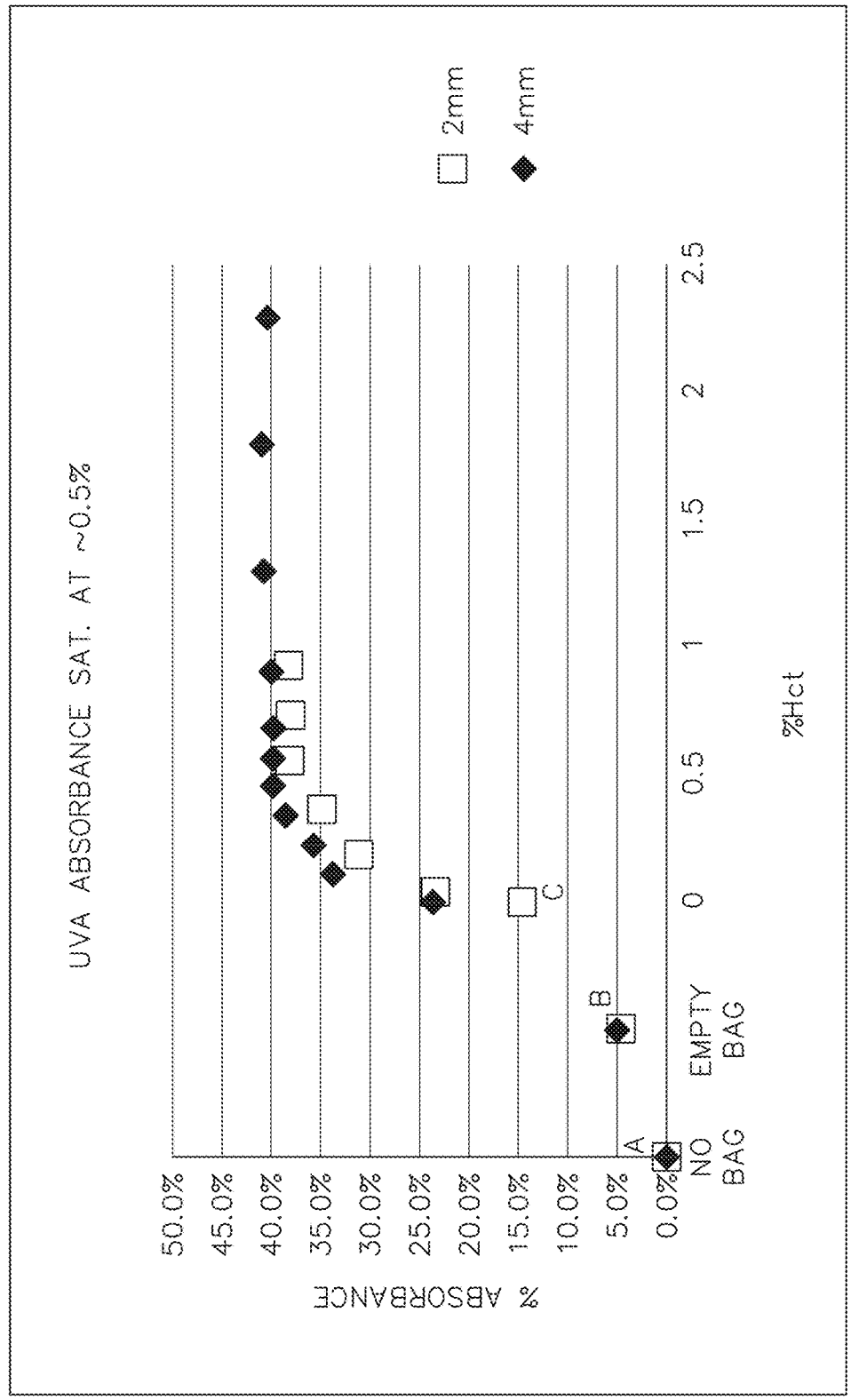
FIG. 6 is a standard absorbance versus hematocrit curve relating percent absorbance of light by the target cell suspension and actual hematocrit of the target cell suspension, according to an exemplary embodiment.
Figure 7:
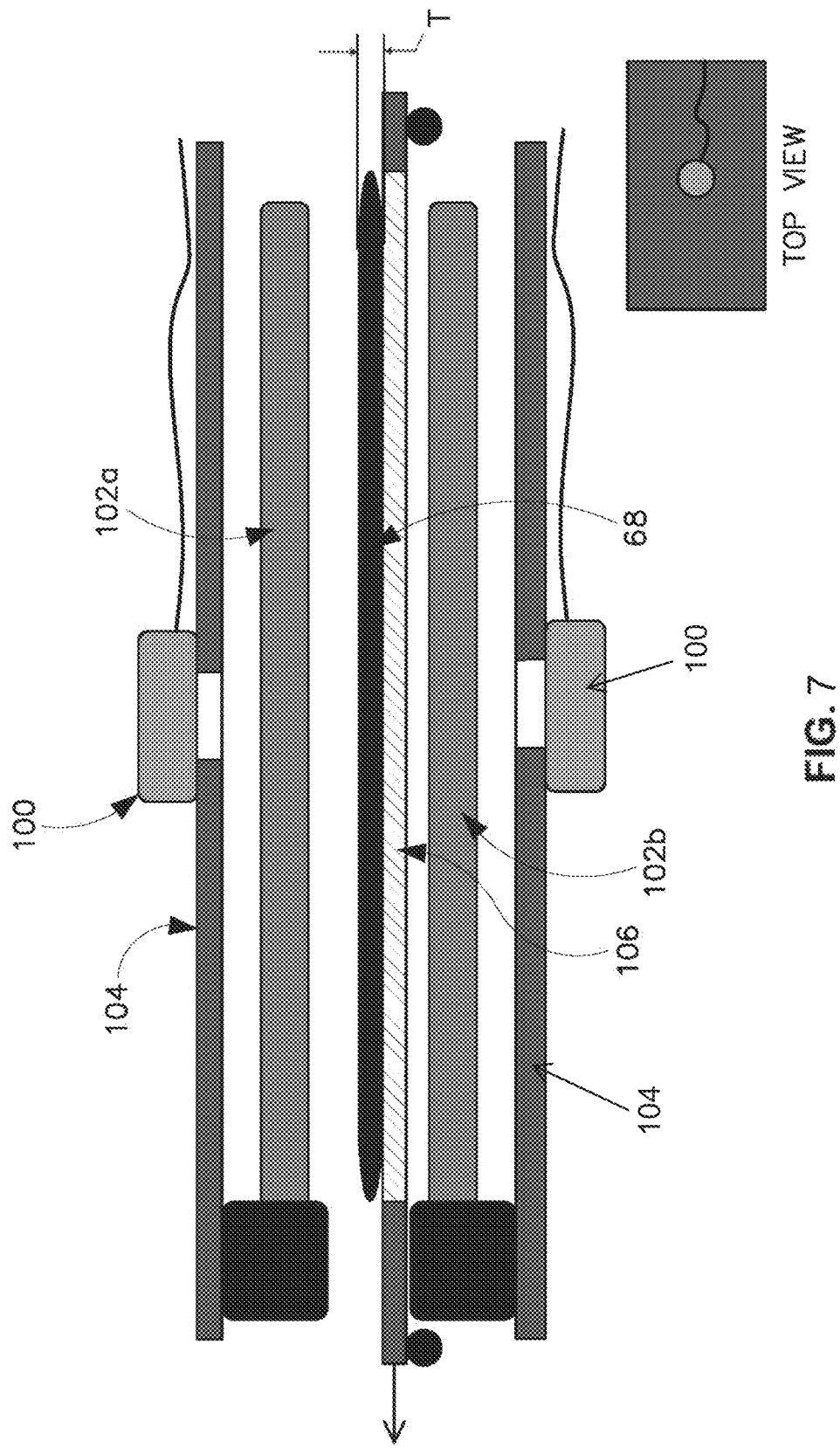
FIG. 7 is a diagrammatic view of a setup used to generate the standard curve of FIG. 6, according to an exemplary embodiment.

Ascertaining an optimal hematocrit suitable for radiation by using a UV-A irradiation receiver may be achieved by plotting a standard absorbance versus hematocrit curve relating percent absorbance of UV-A light by the MNC suspension and actual hematocrit of the MNC suspension, as shown in FIG. 6. The UV-A irradiation receiver (e.g., sensor) 100 used to generate the standard curve may be mounted above an upper bank 102a of a plurality of UV-A light bulbs (i.e., a UV-A transmitter) in an irradiation device, as shown in FIG. 7. A reflector plate 104 may be disposed above the upper bank 102a of light bulbs to reflect light emitted by the bulbs. An exposure plane 106 comprised of UV-transparent material may be disposed below the upper bank 102 of light bulbs to support illumination container 68. A lower bank 102b of a plurality of UV-A light bulbs may be disposed below the exposure plane 106. A second reflector plate 104 may be disposed below the lower bank 102b of light bulbs to reflect light emitted by the light bulbs. A second UV-A irradiation receiver 100 may optionally be mounted below the lower bank 102b of the light bulbs. The irradiation device may include any number of UV-A irradiation receivers 100, depending on the level of accuracy desired, and the UV-A irradiation receivers 100 may be tuned via filters to exclude frequencies of light other than the UV frequency light emitted from the irradiation transmitter to minimize ambient light interference.

A baseline absorbance may be determined by measuring during irradiation UV absorbance in the absence of a MNC suspension or container. Point A of FIG. 6 shows a point at which no container has been loaded within the irradiation device and the UV-A irradiation receiver 100 senses the maximum amount of light emitted, in this example. Point A therefore has been designated as a point at which UV-A light absorbance is 0%, as there is no container within the irradiation device in this example. Point B shows that an empty irradiation container placed on the exposure plane 106 absorbs approximately 5% of the light emitted in this example, as measured by the UV-A irradiation receivers receiving 5% less light than the receivers had received at Point A. Use of other materials in alternative examples may yield other results.

MNC products of varying thickness T with or without RBCs may be tested, as portrayed in FIG. 6 as squares (T=2 mm) and diamonds (T=4 mm). Point C of FIG. 6 shows that UV-A light absorbance is approximately 15% when a MNC suspension containing no RBCs is irradiated. A MNC suspension containing no RBCs may be obtained by performing density-gradient separation (Ficoll) on blood obtained from healthy subjects. The purified MNCs may be suspended in approximately 40% plasma and 60% saline to produce the MNC suspension containing 0% hematocrit (Hct). Known amounts of RBCs may be added to the 0% Hct MNC suspension to obtain suspensions of varying hematocrits while maintaining the intended product thickness T, and the resulting absorbance percentages may be plotted. FIG. 6 shows that the receiver signal saturates when the MNC suspension reaches a Hct level of approximately 0.5%, and the standard curve asymptotes at approximately 40% absorbance.

Testing has revealed that variability in the amounts of light that the target MNCs actually absorb is minimized when the MNC suspension contains a threshold level of RBCs at a given thickness T. An example of such testing is disclosed in International Application Publication WO/2014/123521. Under the parameters and conditions under which the data of FIG. 6 were obtained, this threshold has empirically been shown in this embodiment to be approximately 0.5% Hct for product thicknesses T between 2 and 4 mm. However, in alternative embodiments the threshold may be as little as 0.1% Hct or as great as 10% Hct. Whether a minimum hematocrit has been achieved may therefore be determined by the UV-A irradiation receiver without a hematocrit detector by utilizing the information provided by the standard curve of FIG. 6. The standard curve of FIG. 6 shows that an absorbance level under the asymptotic level of 40% absorbance indicates that the hematocrit is below 0.5%. The ECP system 5 or the irradiation component 20 may be configured via a processing circuit such that when the absorbance level during irradiation as observed by the receiver drops below 40%, a response action may be performed. The response action may comprise the processing circuit terminating the procedure, notifying the operator of below-threshold product, and/or processing additional whole blood in order to increase the MNC product hematocrit. The processing circuit may comprise analog and/or digital electrical components configured or programmed to perform any of the functions described herein. The processing circuit may comprise one or more microprocessors, microcontrollers, application-specific integrated circuits, programmable logic devices, etc., which may further be programmed by way of an operating system, applications, and/or other computer programs stored on a tangible memory device. Memory may comprise RAM, Flash, volatile and/or non-volatile memory of a variety of types used to support processing circuit in executing its functionalities.

The threshold hematocrit may be set to any number that the operator desires. For example, the threshold hematocrit may be configured as 0.25% Hct, in which case the threshold absorbance level may be set to approximately 35%, according to the standard curve of FIG. 6. The threshold absorbance level may also be set to a certain range of deviation from a set number. In the example in which the threshold absorbance level is set to 35%, the range of deviation may be set to, for example, 5% such that a response action is performed when the UV-A irradiation receivers detect absorbance level below 30% or greater than 40%.

An absorbance versus hematocrit curve may be different for each illumination container design or configuration, as well as the irradiation device design or configuration. In the event that a different container design or irradiation device design from the same or different manufacturer is utilized for the ECP procedure, a standard curve for the particular container design and irradiation device design combination may be established with the method disclosed herein.

The embodiments disclosed herein are for the purpose of providing a description of the present subject matter, and it is understood that the subject matter may be embodied in various other forms and combinations not shown in detail. Therefore, specific embodiments and features disclosed herein are not to be interpreted as limiting the subject matter as defined in the accompanying claims.

The invention claimed is:

1. An irradiation device for photopheresis, comprising:
an exposure chamber configured to receive an Illumination container holding a target cell suspension;
an irradiation transmitter configured to irradiate the illumination container and target cell suspension;
an irradiation receiver configured to detect radiation from the irradiation transmitter; and
a processing circuit coupled to the irradiation receiver and configured to detect radiation absorption and to determine whether a hematocrit of the target cell suspension exceeds a predetermined threshold hematocrit and to treat the target cell suspension with a treatment dosage of radiation if the predetermined threshold is exceeded.

2. The irradiation device of claim 1, wherein the irradiation device is configured to elicit a response action if the hematocrit of the target cell suspension does not exceed the predetermined threshold hematocrit, the response action comprising at least one of terminating the photopheresis procedure, generating an error notification; and processing additional cell suspensions to increase hematocrit.

3. The irradiation device of claim 1, wherein the processing circuit is configured to use the irradiation transmitter and irradiation receiver to detect the hematocrit of the target cell suspension and to control the irradiation transmitter to treat the target cell suspension with the treatment dosage of radiation.

4. The irradiation device of claim 3, wherein the processing circuit is configured to use signals from the irradiation receiver to control a magnitude of the treatment dosage of radiation.

5. The irradiation device of claim 1, wherein the irradiation device is part of an online or offline system and wherein the irradiation transmitter transmits UV-A light and the irradiation receiver receives UV-A light.

6. The irradiation device of claim 1, wherein the target cells comprise mononuclear cells and the target cell suspension comprises a photoactivation agent 8-methoxypsoralen.

7. The irradiation device of claim 1, wherein the irradiation transmitter is configured to transmit more than 10 times as much radiation than is actually absorbed by the target cells within the suspension.

8. The irradiation device of claim 1, wherein the irradiation receiver is tuned to exclude frequencies of irradiation other than the UV frequency emitted from the irradiation transmitter of the irradiation device and decrease ambient light interference.

9. The irradiation device of claim 1, wherein the irradiation receiver is disposed within the exposure chamber.

10. A method for detecting hematocrit during an extracorporeal photopheresis procedure, comprising the steps of:
providing an exposure chamber configured to receive an illumination container holding a target cell suspension containing a selected amount of a photoactivation agent;
providing an irradiation device having an irradiation transmitter configured to irradiate contents within the illumination container, wherein the irradiation device contains at least one irradiation receiver;

irradiating the target cell suspension with the irradiation device while detecting hematocrit by analyzing amount of radiation detected by the irradiation receivers; and providing a response action when a hematocrit below a minimum acceptable hematocrit is detected.

11. The method of claim 10, wherein the target cell suspension comprises mononuclear cells and the photoactivation agent comprises 8-methoxypsoralen.

12. The method of claim 10, wherein the irradiation transmitter is configured to transmit more than 10 times as much radiation than is actually absorbed by target cells within the suspension.

13. The method of claim 10, wherein the irradiation device is configured to elicit a response action if the hematocrit of the target cell suspension does not exceed the predetermined threshold hematocrit, the response action comprising at least one of terminating the photopheresis procedure, generating an error notification; and processing additional cell suspensions to increase hematocrit.

14. The method of claim 10, wherein the irradiation device is part of an online system and wherein the irradiation transmitter transmits UV-A light and the irradiation receiver receives UV-A light.

15. The method of claim 10, wherein the irradiation receiver is tuned to exclude frequencies of radiation other than the UV frequency emitted from the irradiation transmitter of the irradiation device and decrease ambient light interference.

16. The method of claim 10, wherein the irradiation receiver is disposed within the exposure chamber.

* * * * *

UNITED STATES PATENT AND TRADEMARK OFFICE
CERTIFICATE OF CORRECTION

| | |
|---|---|
| PATENT NO. | : 10,088,492 B2 |
| APPLICATION NO. | : 14/976950 |
| DATED | : October 2, 2018 |
| INVENTOR(S) | : Christopher J. Wegener et al. |

Page 1 of 1

It is certified that error appears in the above-identified patent and that said Letters Patent is hereby corrected as shown below:

In the Claims

Column 10, Line 13:
"an exposure chamber configured to receive an Hum nation" should be corrected to read "an exposure chamber configured to receive an illumination"

Signed and Sealed this
Twenty-fifth Day of December, 2018

Andrei Iancu
*Director of the United States Patent and Trademark Office*